United States Patent
Wolff

(10) Patent No.: US 10,314,971 B2
(45) Date of Patent: Jun. 11, 2019

(54) METHOD FOR DETECTING AN OCCLUSION IN AN INFUSION LINE

(71) Applicant: Fresenius Vial SAS, Brézins (FR)

(72) Inventor: Rémy Wolff, Morette (FR)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 15/769,654

(22) PCT Filed: Nov. 9, 2016

(86) PCT No.: PCT/EP2016/077033
§ 371 (c)(1),
(2) Date: Apr. 19, 2018

(87) PCT Pub. No.: WO2017/081034
PCT Pub. Date: May 18, 2017

(65) Prior Publication Data
US 2018/0311434 A1 Nov. 1, 2018

(30) Foreign Application Priority Data
Nov. 13, 2015 (EP) .................................. 15306807

(51) Int. Cl.
*A61M 5/168* (2006.01)
*G06F 17/50* (2006.01)

(52) U.S. Cl.
CPC .... *A61M 5/16859* (2013.01); *A61M 5/16831* (2013.01); *G06F 17/5009* (2013.01);
(Continued)

(58) Field of Classification Search
CPC ................................................ A61M 5/16859
See application file for complete search history.

(56) References Cited

U.S. PATENT DOCUMENTS

| 5,242,408 A * | 9/1993 | Jhuboo | A61M 5/1456 604/121 |
|---|---|---|---|
| 2002/0019607 A1 | 2/2002 | Bui | |

(Continued)

FOREIGN PATENT DOCUMENTS

| WO | WO99/52575 A1 | 10/1999 |
| WO | WO 2013/004307 A1 | 1/2013 |
| WO | WO 2013/004308 A1 | 1/2013 |

OTHER PUBLICATIONS

International Search Report and Written Opinion, counterpart International Appl. No. PCT/EP2016/077033, dated Jan. 30, 2017 (9 pages).

*Primary Examiner* — Manuel A Rivera Vargas
(74) *Attorney, Agent, or Firm* — Cook Alex Ltd.

(57) ABSTRACT

A method for detecting an occlusion in an infusion line (3) connected to an infusion device (1) comprises: measuring a force (F) applied to a piston (21) by a pusher device (12) of an infusion device (1) for moving the piston (21) along a movement direction (X) into a cylindrical tube (20) in order to deliver a medical fluid from the cylindrical tube (21) towards an infusion line (3) connected to the cylindrical tube (20); calculating, from the measured force (F), a value indicative of a pressure (P) in the cylindrical tube (20), wherein for calculating said value indicative of said pressure (P) a frictional force value (F0) indicative of a friction of the piston (21) relative to the cylindrical tube (20) is taken into account; and comparing said value indicative of said pressure (P) to a threshold value to determine whether an occlusion is present in the infusion line (3). Herein, the frictional force value (F0) is determined using a mathematical model modelling the friction of the piston (21) relative to the cylindrical tube (20) in dependence on the position of the piston (21) relative to the cylindrical tube (20) along the movement direction (X) and in dependence on the velocity (Continued)

by which the piston (21) is moved relative to the cylindrical tube (3). In this way a method for reliably detecting an occlusion in an infusion line during an infusion process is provided.

16 Claims, 10 Drawing Sheets

(52) U.S. Cl.
CPC .............. *A61M 2005/16863* (2013.01); *A61M 2205/18* (2013.01); *A61M 2205/332* (2013.01); *A61M 2205/50* (2013.01)

(56) References Cited

U.S. PATENT DOCUMENTS

| | | |
|---|---|---|
| 2006/0184154 A1 | 8/2006 | Moberg et al. |
| 2007/0191770 A1 | 8/2007 | Moberg et al. |
| 2010/0214110 A1 | 8/2010 | Wang et al. |

* cited by examiner

METHOD FOR DETECTING AN OCCLUSION IN AN INFUSION LINE

The present application is a U.S. National Stage of PCT International Patent Application No. PCT/EP2016/077033, filed Nov. 9, 2016, which claims priority to EP Application No. 15306807, filed Nov. 13, 2015, both of which are hereby incorporated herein by reference.

The invention relates to a method for detecting an occlusion in an infusion line according to the preamble of claim 1.

In a method for detecting an occlusion in an infusion line of this kind a force applied to a piston by a pusher device of an infusion device for moving the piston along a movement direction into a cylindrical tube in order to deliver a medical fluid from the cylindrical tube towards an infusion line connected to the cylindrical tube is measured. From the measured force a value indicative of a pressure in the cylindrical tube is calculated, wherein for calculating said value indicative of said pressure a frictional force value indicative of a friction of the piston relative to the cylindrical tube is taken into account. By comparing said value indicative of said pressure to a threshold value it can then be determined whether an occlusion is present in the infusion line or not.

Medication in a fluid state can be infused into a patient using an infusion line. The infusion line is connected to a fluid source such as a syringe that stores the medication. The medication can be pushed out of the syringe through the infusion line towards the patient using a pusher device of an infusion device such as a syringe pump acting onto the syringe for continuously pushing a piston into a cylindrical tube in order to deliver medication from the cylindrical tube of the syringe via the infusion line towards the patient.

During such an infusion process an occlusion may occur in the infusion line, which, in some cases, may cause severe injury to the patient. There hence is a need to reliably detect an occlusion occurring in an infusion line, in order to avoid injuries resulting from occluded infusion lines.

From the state of the art methods for detecting an occlusion in an infusion line during an infusion process are known that are based on the assumption that an occlusion causes a raise of the pressure in the infusion line. An increased pressure in turn causes the force to be applied to the syringe by a means of pumping device for pushing the medication through the infusion line towards the patient to increase. By monitoring the force applied to the syringe, hence, the actual pressure in the infusion line can be deduced and accordingly, if the actual pressure exceeds a threshold value, an alarm signal indicative of an occlusion can be triggered.

More sophisticated methods additionally take into account the frictional force of the syringe, such as the frictional force between the piston and the cylindrical tube of the syringe, when the piston is moving in the cylindrical tube. Indeed the total force required to push the liquid through an infusion line comprises a frictional force component, resulting from the friction occurring when the piston is moved in the cylindrical tube, and a pressure component resulting from the pressure in the infusion line. In some methods known in the art, the frictional force is assumed to be constant during the infusion process. For a given syringe type a constant value is then preset for the frictional force. For calculating the pressure inside the infusion line, hence, the force applied to the syringe is thus corrected for the frictional force using a constant value.

However, the frictional force is not necessarily constant for all syringes of a specific syringe type and/or throughout the entire infusion process, but can vary for example over the length of the cylindrical tube in which the piston is longitudinally moved. For example, if the internal diameter of the cylindrical tube slightly decreases when moving the piston in the cylindrical tube, the frictional force between the piston and the inner wall of the cylindrical tube will increase and vice versa. In addition, the inner surface of the cylindrical tube may have varying characteristics over the length of the cylindrical tube. If the variation of the frictional force resulting therefrom is not taken into account and the true frictional force is higher than the preset (constant) value for the frictional force, the true pressure in the infusion line is smaller than the determined pressure. An overpressure may thus be detected which truly is not present, possibly leading to a false alarm. On the other hand, if the true frictional force is smaller than the preset (constant) value for the frictional force, the true pressure in the infusion line is higher than the determined pressure, in which case an overpressure resulting from an occlusion in the infusion line may not be detected.

The reliability of a method for detecting an occlusion that presumes that the frictional force component throughout the infusion process is constant is thus limited. However, a reliable method for detecting an occlusion may be of particular relevance, especially in neonate and pediatric care.

It is an object of the instant invention to provide a method for reliably detecting an occlusion in an infusion line during an infusion process.

This object is achieved by the method for detecting an occlusion in an infusion line during an infusion process comprising the features of claim 1.

Accordingly, the frictional force value is determined using a mathematical model modelling the friction of the piston relative to the cylindrical tube in dependence on the position of the piston relative to the cylindrical tube along the movement direction and in dependence on the velocity by which the piston is moved relative to the cylindrical tube.

The frictional force value hence is determined using a mathematical model. Typically, the frictional force value may depend on
- the syringe size, brand, model and batch,
- the pushing velocity,
- the position of the piston on its full travel range,
- the temperature,
- the waiting time between syringe preparation and the start of an infusion process,
- the liquid used for infusion, and
- the pressure in the syringe.

The different factors herein have a different impact on the frictional force, wherein it generally can be assumed that the syringe size, brand, model and batch as well as the pushing velocity and the position of the piston relative to the cylindrical tube of the syringe have the largest influence.

The model hence aims at modelling the frictional force in particular in dependence on the velocity and the position, wherein the modelling, in one embodiment, may be such that particular characteristics of a particular syringe used for an infusion process are taken into account for modelling the frictional force in dependence on the velocity and the position.

Herein, characteristic parameters for a syringe having an influence on the frictional force in dependence of the velocity and the position may be stored in a database of the infusion device, such that the model can be adjusted for a particular syringe used on an infusion device for computing the frictional force in dependence on the velocity and the position of the piston relative to the cylindrical tube of the syringe during an infusion process.

The model is used to obtain an estimate of a frictional force value dependent on the position of the piston relative to the cylindrical tube along the movement direction and dependent on the velocity by which the piston is moved relative to the cylindrical tube during an infusion process. The velocity herein is directly linked to the flow rate which shall be achieved during an infusion process, i.e. the rate at which a fluid contained in the cylindrical tube is to be administered to the patient.

The model, in one embodiment, may for example include a velocity dependent term modelling the dependence of the frictional force on the velocity of the piston relative to the cylindrical tube and a position dependent term modelling the dependence of the frictional force on the position of the piston relative to the cylindrical tube.

For example, the frictional force value for a position i may be determined according to the following equation:

$$F_0(i)=F_{pr}+(F_{0,velocity}-F_{pr}) \cdot Pos\_coef(i)$$

Herein, $F_0(i)$ denotes the frictional force value at the position i. $F_{pr}$ denotes a preload force. $F_{0,velocity}$ denotes the velocity dependent term, and $Pos\_coef(i)$ denotes the position dependent term.

Generally, the velocity dependent term depends on the velocity by which the piston is moved relative to the cylindrical tube. At a constant flow rate during an infusion process the velocity of the piston will be constant, and the velocity dependent term assumes a value associated with this velocity.

The position dependent term in turn varies with position. The variation herein is largely influenced by the variation of the friction of the piston within the cylindrical tube, for example due to geometrical changes of the cylindrical tube along the travel range of the piston inside of the cylindrical tube.

The velocity dependent term may be computed for example using an equation including terms for a Coulomb friction, a Stribeck friction and/or a viscous friction. For example, the velocity dependent term may be modelled according to the following equation:

$$F_{0,velocity}=F_C+(F_{brk}-F_C) \cdot e^{(-C_v \cdot v)}+f_{vfr} \cdot v$$

Herein, $F_C$ is a coulomb friction force, $F_{brk}$ is a breakaway friction force, $C_v$ is a transition approximation coefficient, v is the velocity, and $F_{vfr}$ is a viscous friction coefficient.

The coulomb friction can be computed by the relation $$F_C=F_{pr}+f_{cfr} \cdot P$$

wherein $F_{pr}$ is the preload force, $f_{cfr}$ is the coulomb friction coefficient, and P is the pressure. Assuming that the pressure P has no impact on the friction force, this relation can be simplified to $$F_C=F_{pr}$$

such that the coulomb friction force $F_C$ equals the preload force $F_{pr}$.

The above stated equation for the velocity dependent term can be simplified by neglecting the viscous effect due to the viscous friction coefficient $f_{cfr}$ and by linearizing the second term indicating the Stribeck friction.

Hence, one arrives at a relation in which the velocity dependent term assumes a constant value for a velocity below a first velocity value and/or for a velocity above a second velocity value. Within the range in between the first velocity value and the second velocity value it then can be assumed that the velocity dependent term changes linearly. This mathematically can be expressed as follows:

if v [mm/h]<$v_{transit}$ [mm/h] then $$F_{0,velocity}[gf]=F_{brk}[gf]$$

if v [mm/h] $\in [v_{transit}$[mm/h], $v_{max}$[mm/h]] then $$F_{0,velocity}[gf]=F_{pr}+a[gf/(mm/h)] \cdot v[mm/h]+b[gf]$$

where $$\begin{cases} a[gf/(mm/h)] = \dfrac{F_{brk}[gf] - F_{pr}[gf]}{v_{transit}[mm/h] - v_{max}[mm/h]} \\ b[gf] = -a[gf/(mm/h)] \cdot v_{max}[mm/h] \end{cases}$$

if v[mm/h]>$v_{max}$[mm/h] then $$F_{0,velocity}[gf]=F_{pr}[gf]$$

The position dependent term changes with position and may be expressed simply by a list of coefficients. The coefficients can be defined for a multiplicity of discrete position values, wherein it can be interpolated between discrete positions to obtain a coefficient value for a position in between two neighboring discrete positions.

By multiplying the position-dependent coefficient with a term including the velocity dependent term, the position dependent frictional force value is obtained as already stated above according to the following relation:

$$F_0(i)=F_{pr}+(F_{0,velociy}-F_{pr}) \cdot Pos\_coef(i)$$

The frictional force value at a specific position determined in this way can be used to calculate the pressure within the cylindrical tube, which corresponds to the pressure in the infusion line. By comparing the pressure (or generally a value indicative of the pressure) to a predefined threshold value it can then be determined whether an occlusion has occurred, such that an alarm can be triggered.

The parameters stated above, for example the Coulomb friction coefficient, the viscous friction coefficient, the breakaway friction force and the preload force, depend on the particular syringe used on the system. Hence, the system may store different parameters for different syringes, such that the model can use the specific parameters applicable for a particular syringe used on the system for an infusion process.

The object is also achieved by the method comprising the features of claim 7. The method comprises:

determining, at a current position of the piston, a slope value associated with the measured force at the current position of the piston as the piston is moved along the movement direction, and if the slope value lies within a predetermined range, assuming that the frictional force value is equal to the measured force at a position prior to the current position for calculating said value indicative of said pressure.

Hence, within the method the frictional force value is not determined using a model, but directly determined from the measured force. Herein, it generally is assumed that the frictional force value is equal to the measured force if no occlusion is present on the infusion line. Thus, it is assumed that the pressure within the infusion line is zero if no occlusion is present, such that the measured force is substantially due to friction experienced by the piston as the piston is moved in the cylindrical tube.

As the piston is moved in the cylindrical tube, a slope value associated with the measured force at the current position is calculated and monitored. If it is found that the slope value falls into a predetermined range bounded by a minimum slope and a maximum slope, it is assumed that a rise in the measured force (indicated by the slope) is not due to the frictional force and its variation, but likely is due to an occlusion on the infusion line. Hence, if it is found that the slope value falls into the predetermined range, the frictional force value is no longer set to the measured force, but the frictional force value is set to a measured force value which was obtained at a position prior to the current position. The frictional force value hence no longer tracks the measured force, but is held fixed at the measured force value at a position prior to the current position.

In one embodiment, said position prior to the current position equals the position at which the slope value last was outside of the predetermined range. Hence, if it is first found that the slope of the measured force falls into the predetermined range, the frictional force value is held fixed at the measured force value for the position immediately prior to the current position (for which the slope did not fall into the range), and is held fixed at this measured force value as long as the slope of the measured force remains within the predetermined range for subsequent measurements at subsequent positions.

In this regard it is to be noted that the measured force is generally measured at discrete intervals, for example at discrete positions or at discrete measurement times. Herein, since the piston is moved continuously relative to the cylindrical tube, a measurement time relates to a specific position, such that generally one can be interchanged with the above.

The slope value generally can be determined as the derivative of the measured force. This can be computed for example by taking the difference of the measured force at the current position and the measured force at a position prior to the current position, for example at a position immediately prior to the current position, i.e. the last measurement position prior to the current position.

If it is found that the slope does not fall into the predetermined range, it is assumed that no occlusion is present, and hence the frictional force value is assumed to equal the measured force at the current position of the piston. Hence, the frictional force value tracks the measured force, assuming that the measured force substantially is due to friction occurring when moving the piston relative to the cylindrical tube.

The instant method is based on the finding that for a particular system using a particular syringe in connection with a particular infusion line the pressure inside the line will rise at a specific slope determined by the characteristics of the infusion line and the syringe. Hence, by observing the slope, it can be determined whether the slope of the measured force is close to the slope that is expected in case of an occlusion or not. Hence, by monitoring whether the slope of the measured force falls into a range around the expected slope, it in principle can be detected whether an occlusion is present or not.

In this regard, if the slope of the measured force is below the predetermined range, it can be assumed that no occlusion is present, as the pressure in the infusion line does not rise excessively. If the slope of the measured force is above the predetermined range, it can be assumed that the rise of the slope is not due to an occlusion, but it is due to other factors, for example to other devices or means causing a pressure change within the system, for example when a second infusion device is present in the system.

The predetermined range is generally determined by a tolerance range around the expected slope, and hence is bound by a minimum slope smaller than the expected slope and a maximum slope larger than the expected slope.

The expected slope herein can be computed taking characteristics of the system into account. Characteristics can be stored for example in a database of the infusion device, such that the expected slope can be computed prior to the start of an infusion process when a particular syringe in connection with a particular infusion line is to be used for an infusion process and correspondingly is identified to the system by user, for example a nurse.

The expected slope is for example influenced by the compliance of the cylindrical tube, the compliance of the infusion line, a stiffness of the pusher device and/or a dimension of the cylindrical tube. The compliance herein indicates a measure for the expansibility of the system, for example the expansibility of the cylindrical tube of the syringe used on the infusion device or the expansibility of the infusion line connected to the cylindrical tube. Generally, the compliance indicates the change of volume for a change in pressure and accordingly is stated for example in ml/bar. With respect to for example the infusion line, the compliance indicates by what volume the infusion line expands if the pressure increases by a certain margin.

For different syringes and different infusion lines, different characteristic values, for example compliance values, can be stored in the system, such that a particular set of values is chosen to compute the expected slope if a particular syringe in connection with a particular infusion line is to be used for an infusion process.

Herein, also the minimum slope bounding the predetermined range at its lower end and the maximum slope bounding the predetermined range at its upper end can be determined from those characteristics.

In one embodiment, a prealarm is triggered if the slope value lies within a predetermined range. The predetermined range herein may be equal to the aforementioned range which is used to determine the frictional force value. It however is also possible that the predetermined range triggering the prealarm differs from the range with which the slope value is compared for determining the frictional force value.

This aspect is based on the finding that an alarm may be triggered from the comparison of the slope value with an expected slope alone. If the slope value is within a tolerance range about the expected slope value, this may indicate that an occlusion has occurred.

This comparison may trigger a prealarm, i.e. a warning prior to an actual occlusion alarm, to warn a user at an early stage that an occlusion has occurred.

This method in principle can be employed also independently from the above noted method. In this case a method for detecting an occlusion in an infusion line connected to an infusion device generally comprises:

measuring a force applied to a piston by a pusher device of an infusion device for moving the piston along a movement direction into a cylindrical tube in order to deliver a medical fluid from the cylindrical tube towards an infusion line connected to the cylindrical tube, determining, at a current position of the piston, a slope value associated with the measured force at the current position of the piston as the piston is moved along the movement direction, and if the slope value lies within a predetermined range, triggering an alarm.

As described above, as the piston is moved in the cylindrical tube, a slope value associated with the measured force at the current position is calculated and monitored. If it is found that the slope value falls into a predetermined range bounded by a minimum slope and a maximum slope, it is assumed that a rise in the measured force (indicated by the slope) is not due to a frictional force and its variation, but likely is due to an occlusion on the infusion line. Hence, if it is found that the slope value falls into the predetermined range, it is assumed that an occlusion is present and an alarm is triggered accordingly.

The slope value generally can be determined as the derivative of the measured force. This can be computed for example by taking the difference of the measured force at the current position and the measured force at a position prior to the current position, for example at a position immediately prior to the current position, i.e. the last measurement position prior to the current position.

If it is found that the slope value does not fall into the predetermined range, it is assumed that no occlusion is present, and hence no alarm is triggered, or an alarm which has been triggered before is cancelled.

The methods described above can be used by themselves to determine whether an occlusion is present on an infusion line or not. Hence, each method by itself can be implemented in an infusion device, and can be used to monitor an infusion process in order to trigger an alarm in case it is found that an occlusion may be present on the infusion line.

In a beneficial embodiment, the methods however are used in combination. Hence, both methods are implemented on an infusion device, and during an infusion process both methods are used to determine an estimate of the frictional force in order to monitor whether an occlusion may be present on an infusion line or not. In this way a robust technique is provided for detecting an occlusion. In particular, in certain scenarios one method may be more sensitive than the other, such that it is made sure that an occlusion is reliably detected by using the methods in combination.

Herein, an alarm may be triggered if it is determined with at least one of said methods that said value indicative of the pressure is above said threshold value. Hence, the frictional force value is determined by both methods, and by using the two different frictional force values determined by the two methods, two estimates of the pressure inside the infusion line are derived. By comparing these estimates of the pressure to the predefined threshold value, it can be determined whether, at least for one method, it is found that an occlusion is present on the infusion line.

The idea underlying the invention shall subsequently be described in more detail with respect to the embodiments shown in the figures. Herein:

Figure 3:
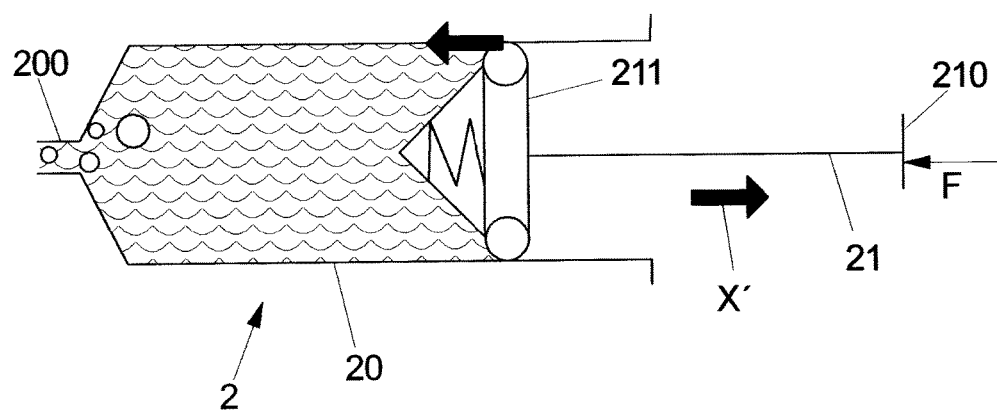
Figure 4:
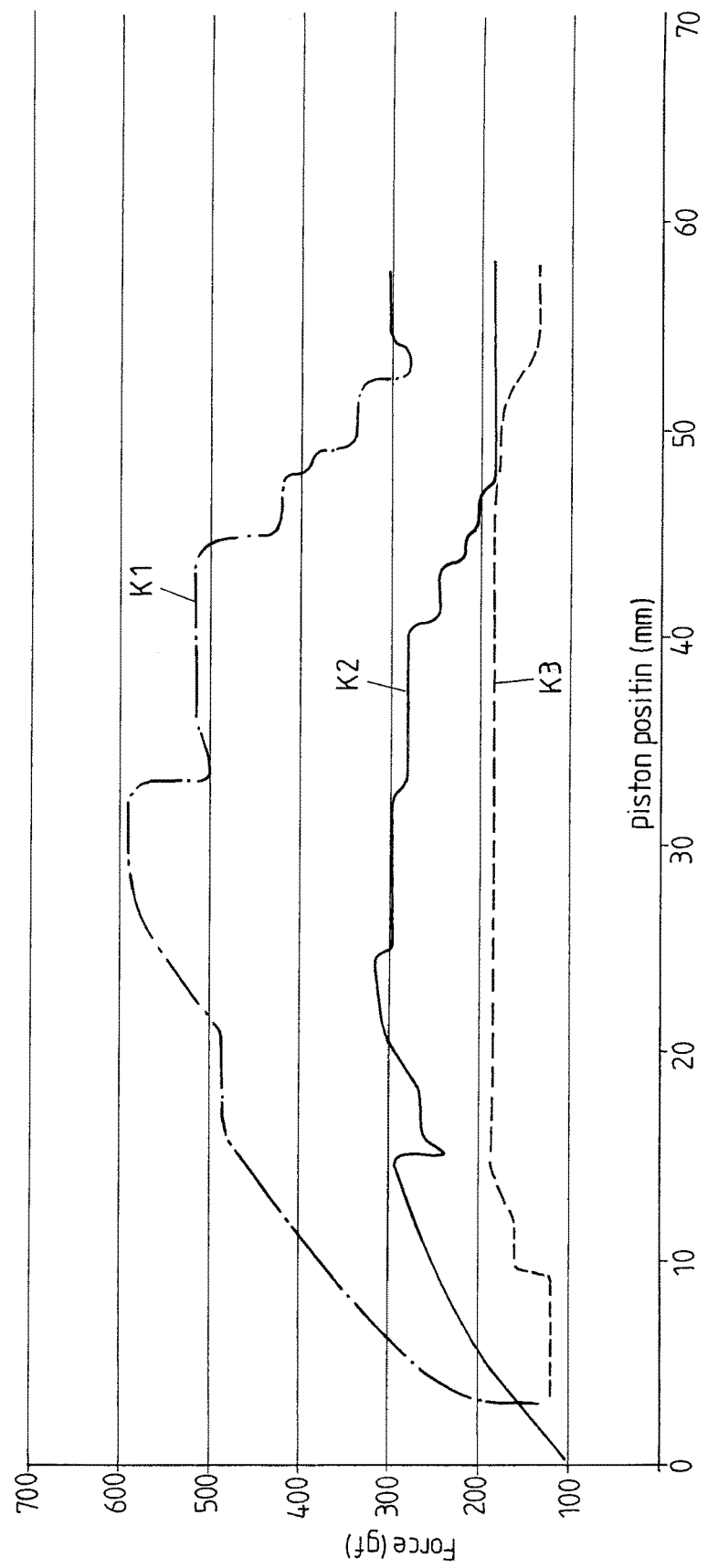
Figure 5:
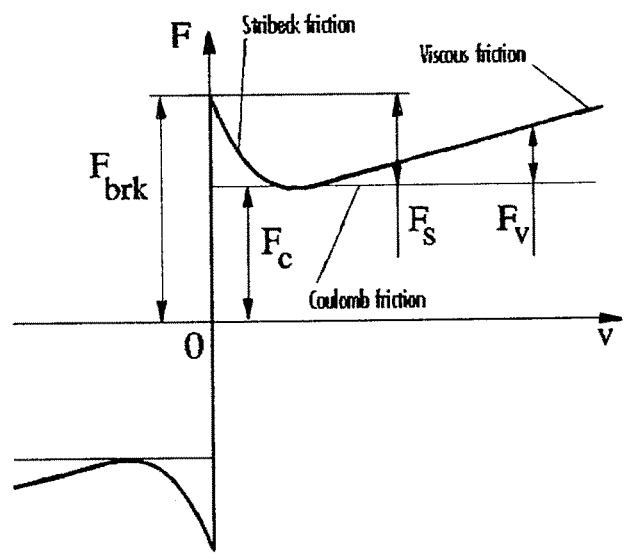
Figure 6:
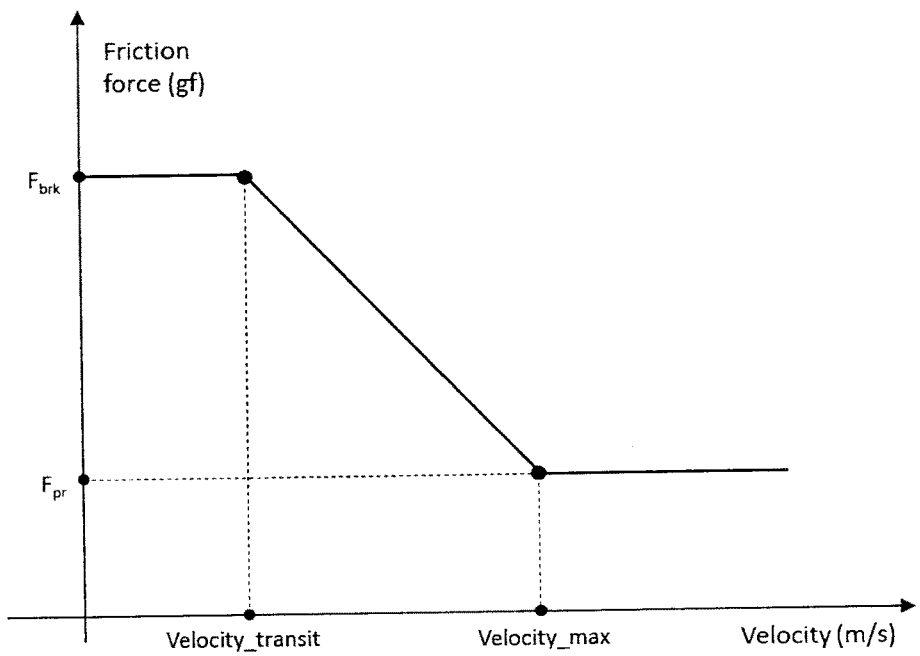
Figure 7A:
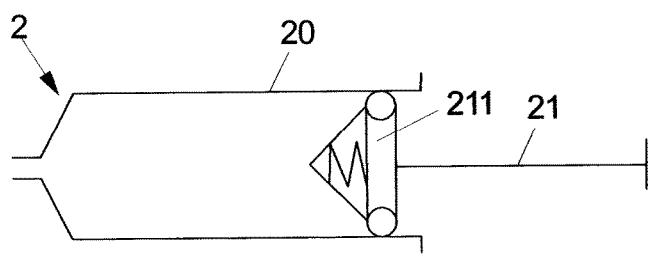
Figure 8A:
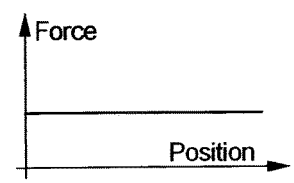
Figure 7B:
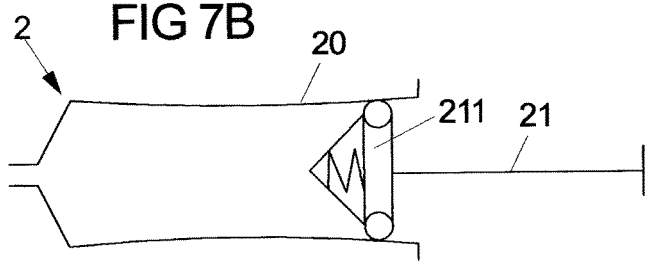
Figure 8B:
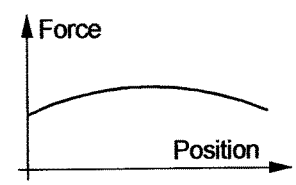
Figure 7C:
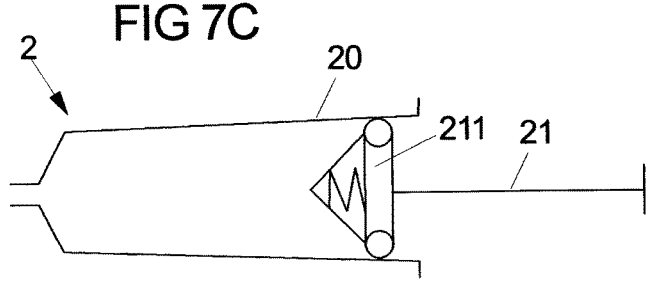
Figure 8C:
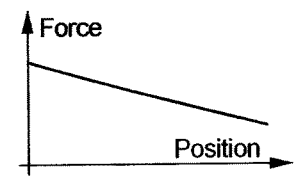
Figure 7D:
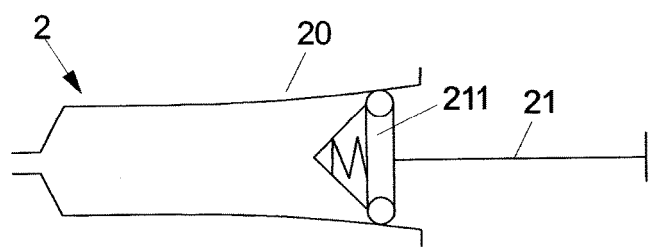
Figure 8D:
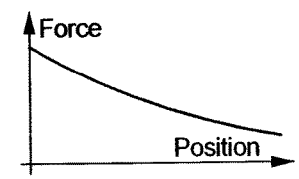
Figure 9:
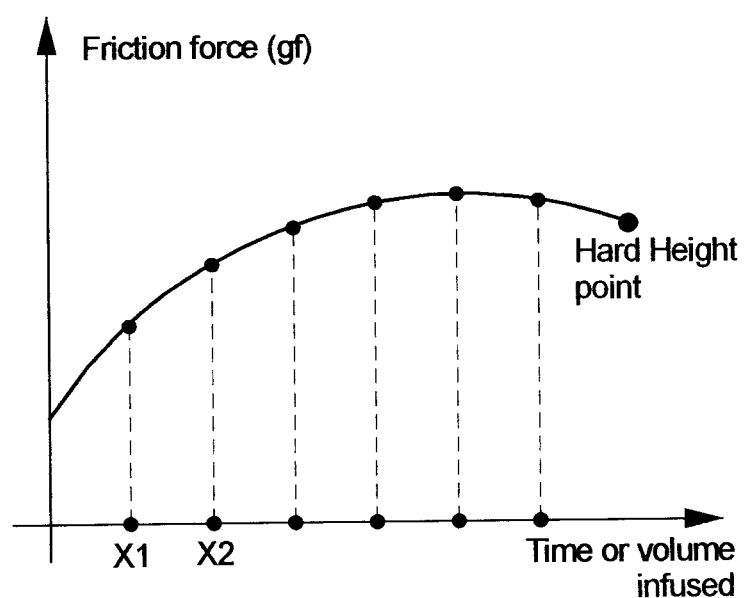
Figure 10:
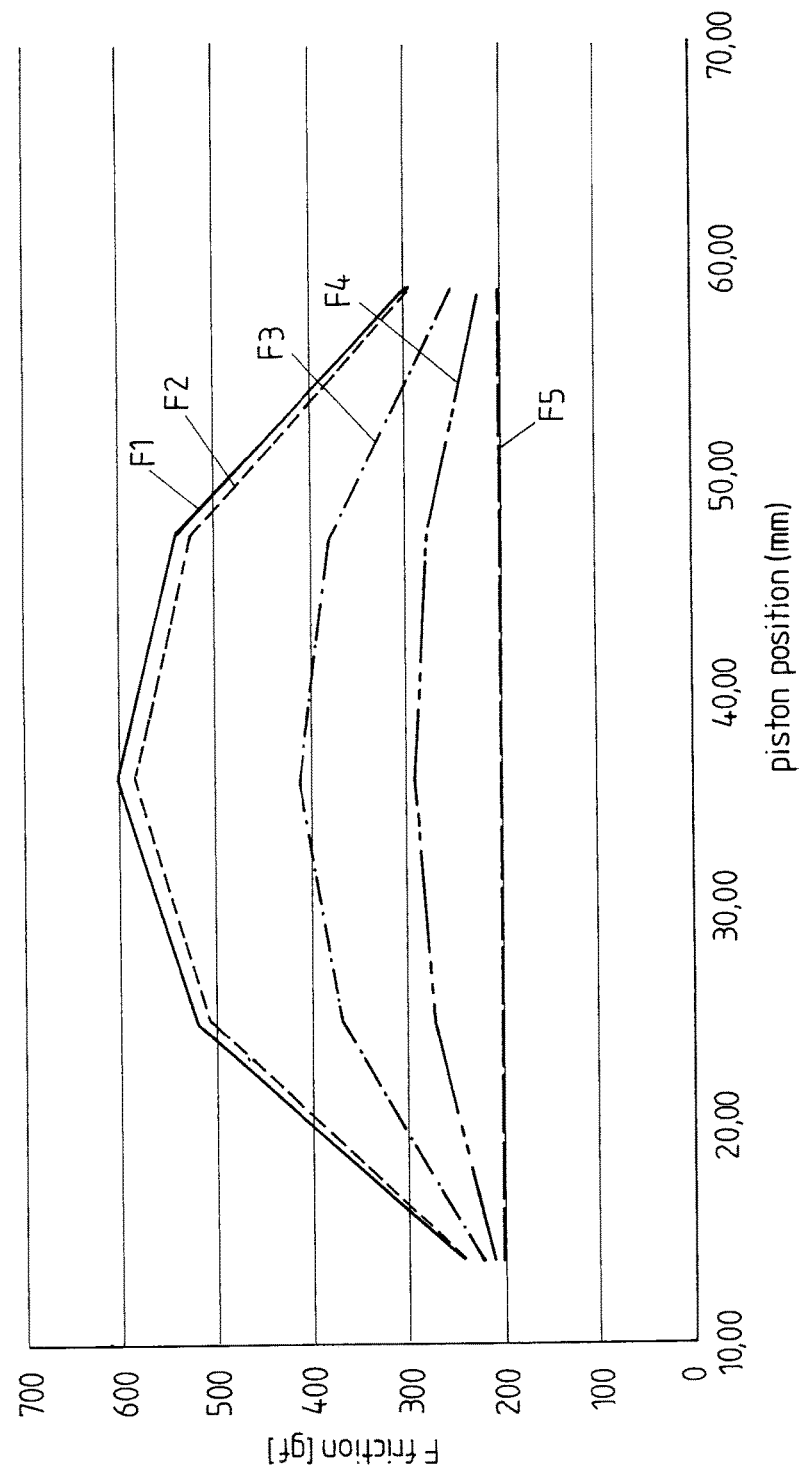
Figure 11:
Figure 12:
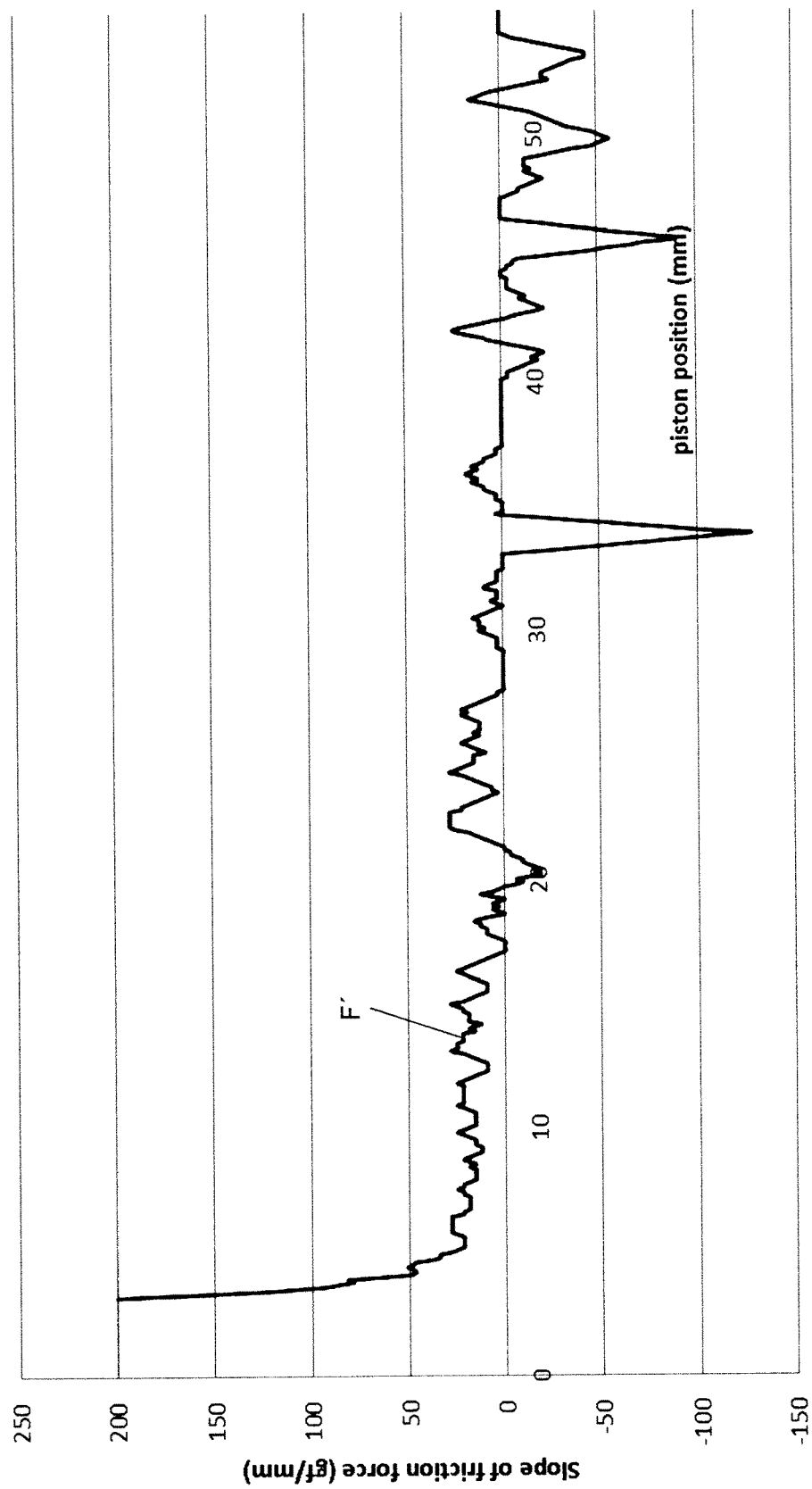
Figure 13:
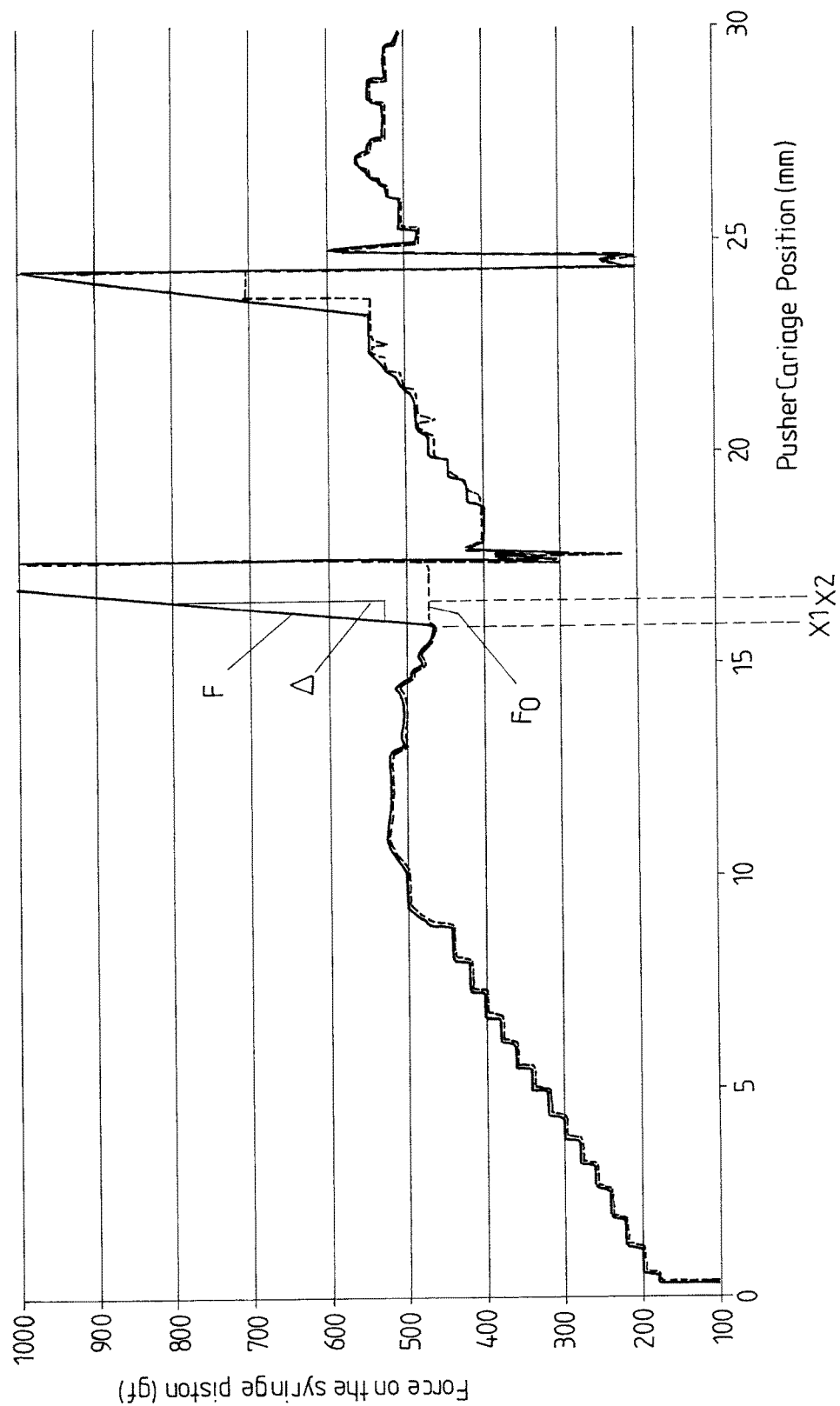

FIG. 3 a schematic view of the syringe, as the piston is moved out of the cylindrical tube;

FIG. 4 a graphical view of a measured force as a function of the position, for different velocities by which the piston is moved relative to the cylindrical tube;

FIG. 5 a graphical view of the dependence of the frictional force on the velocity;

FIG. 6 a view of a linearized model of the frictional force in dependence on the velocity;

FIG. 7A-7D schematic views of different syringes having different characteristics;

FIG. 8A-8D graphical views of the frictional force dependent on the position for the different syringes according to FIG. 7A to 7D;

FIG. 9 a view of a simplified dependence of the frictional force on the position;

FIG. 10 a view of the modelled frictional force in dependence on the position, for different velocities;

FIG. 11 a view of the measured force over position;

FIG. 12 a view of the derivative of the measured force according to FIG. 11; and FIG. 13 a view of the measured force in the occurrence of an occlusion.

Figure 1:
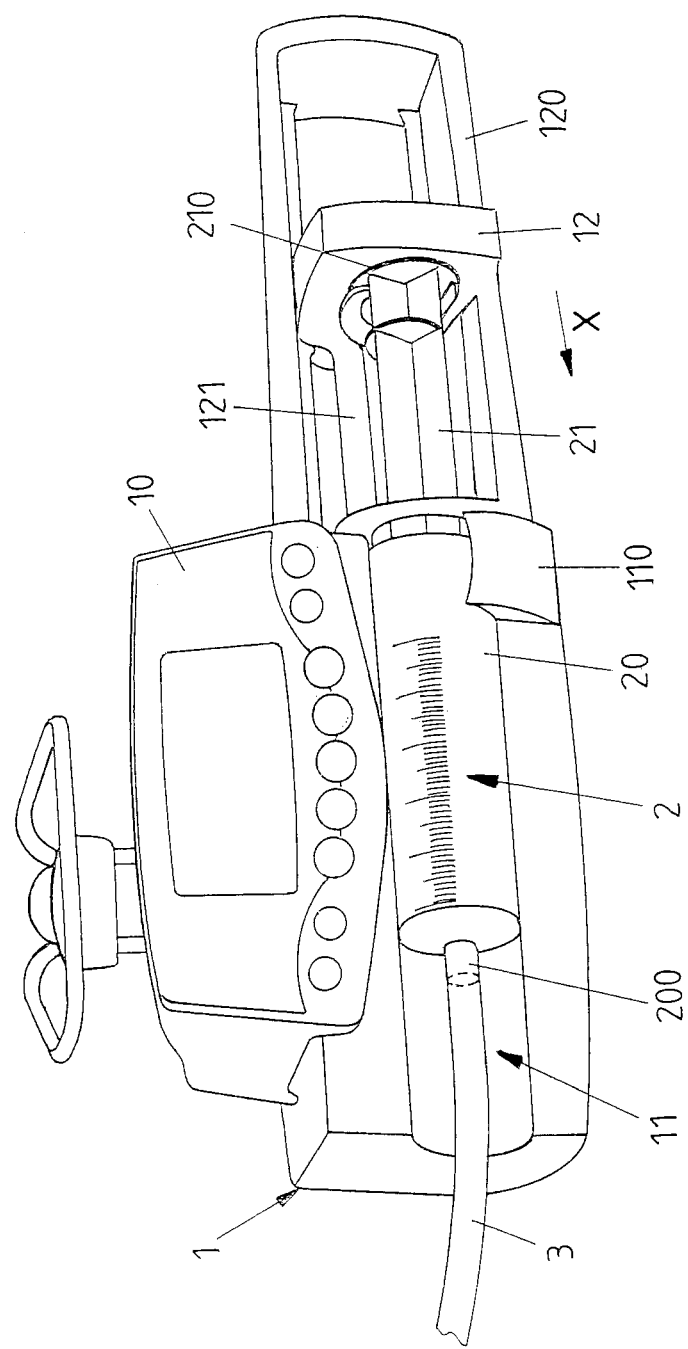
FIG. 1 shows a view of an embodiment of an infusion device in the shape of a syringe pump.

FIG. 1 shows an infusion device 1 in the shape of a syringe pump having a housing 10 and a receptacle 11 arranged on the housing 10 to receive a syringe 2 therein.

The syringe 2 comprises a cylindrical tube 20 which, when installing the syringe 2 on the infusion device 1, contains a medical liquid, for example a medication or a solution for the parenteral feeding, to be infused to a patient. The cylindrical tube 20 is connected, via a connector 200, to an infusion line 3 which may extend from the syringe 2 towards a patient for infusing the medical liquid to the patient.

For installing the syringe 2 on the receptacle 11 of the infusion device 1, the cylindrical tube 20 of the syringe 2 is placed in the receptacle 11 and is mechanically connected to the housing 10 by means of a fixation device 110. By means of the fixation device 110, for example constituted by a releasable clamp element, the cylindrical tube 20 is secured within the receptacle 11 such that the cylindrical tube 20 is held in position on the receptacle 11.

The syringe 2 comprises a piston 21 which, for delivering medical fluid contained in the cylindrical tube 20, can be pushed into the cylindrical tube 20 in a pushing direction X. For this, the infusion device 1 comprises a pusher device 12 movably arranged within a guide device 120 and connected to a suitable drive mechanism via a connecting rod 121.

For operating the infusion device 1, the syringe 2 is installed on the infusion device 1 and, for performing an infusion process, the pusher device 12 is electrically moved in the pushing direction X to move the piston 21 into the cylindrical tube 20 for delivering the medical fluid contained in the cylindrical tube 20 via the infusion line 3 towards the patient.

Generally, if during an infusion process an occlusion occurs on the infusion line 3 connected to the cylindrical tube 20 of the syringe to, the pressure in the infusion line will rise. To detect an occlusion, hence, the pressure in the infusion line 3 can be observed, and when an abnormal rise in pressure is found it can be concluded that an occlusion is present.

To observe the pressure in the infusion line 3, the force F applied to the piston head 210 of the piston 21 by means of the pusher device 12 is measured by a sensor placed in between the pusher device 12 and the piston head 210. The force F measured in this way allows for an indirect measurement of the pressure within the cylindrical tube 20, which generally equals the pressure in the infusion line 3.

In particular, the pressure in the cylindrical tube 20 depends on the measured force F according to the following relation:

$$P = \frac{F - F_0}{S}.$$

Herein, P denotes the pressure, F denotes the measured force, $F_0$ denotes a frictional force component and S denotes the effective surface by which the piston 21 acts onto the liquid contained in the cylindrical tube 20. The effective surface S is substantially determined by the inner diameter of the cylindrical tube 20.

By determining the pressure P in this way and by comparing the determined pressure P to a predefined threshold $P_{thres}$ it can then be concluded whether an occlusion is present in the infusion line 3 or not. In particular, if it is found that the pressure P rises above the threshold $P_{thres}$, it is concluded that an occlusion is present.

Whereas F is measured and S is known from the geometrical dimensions of the cylindrical tube 20 of the syringe 2, the frictional force component $F_0$ cannot be determined in an easy way. In particular, the frictional force component $F_0$ may vary in dependence on the specific syringe 2 used on the system, wherein the frictional force component $F_0$ generally is dependent on the position of the piston 21 within the cylindrical tube 20 and on the velocity by which the piston 21 is moved relative to the cylindrical tube 20 during an infusion process.

The methods described subsequently deal with the determination of the frictional force component $F_0$. Herein, within a first method a model-based approached is used to determine the frictional force component $F_0$. In a second method an approach based on measurements is used, assuming that the frictional force component $F_0$ equals the measured force as long as no occlusion is present in the system.

Figure 2:
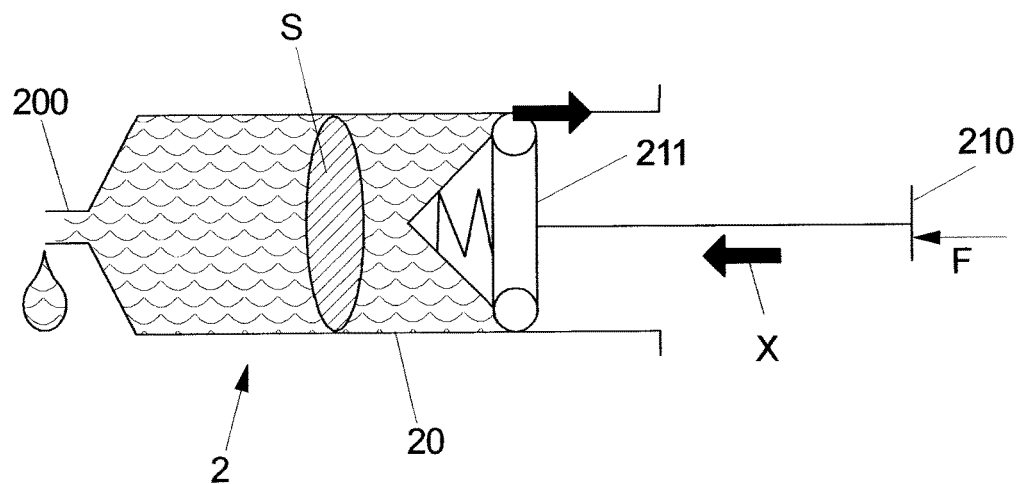
FIG. 2 shows a schematic view of a syringe comprising a cylindrical tube and a piston moved into the cylindrical tube for pushing a liquid contained in the cylindrical tube towards an infusion line.

Generally, if the pusher device 12 acts onto the piston 21 in the pushing direction X to push the piston 21 into the cylindrical tube 20, as schematically shown in FIG. 2, the force F acting onto the piston 21 and measured at the piston head 210 relates to the pressure as follows:

$$F = P \cdot S + F_0$$

Herein, P is the pressure inside the cylindrical tube 20 of the syringe 2 (in mbar), S is the effective surface determined by the inner diameter of the syringe (in mm$^2$), and $F_0$ is the frictional force between the moving part of the syringe (the piston 21) and the fixed part (the cylindrical tube 20).

When the piston 21 is instead moved backwards (for example during an occlusion release) in the opposite direction X' as indicated in FIG. 3, the force F relates to the pressure as follows:

$$F = P \cdot S - F_0$$

Generally, F is measured during an infusion process by a sensor in between the pusher device 12 and piston head 210. The effective surface S is stored in a database of the infusion device 1 (generally, the inner diameter of the syringe will be registered in the pump such that by identifying the syringe prior to an infusion process the surface S can be determined).

The frictional force component $F_0$ depends at least on the following parameters (sorted approximately by their relevance for the frictional force):
the syringe brand, model and batch
the pushing velocity,
the position of the piston on its full travel range,
the temperature,
the waiting time between syringe preparation and infusion start,
the liquid inside the syringe, and
the pressure.

It is to be noted that the catheter size, the extension line diameter and length and the drug viscosity generally can be considered to have no influence on the frictional force. But these parameters may of course have an influence on the pressure.

In the following, two methods are described, providing different approaches to obtain an estimate of the frictional force $F_0$ in dependence on the velocity by which the piston 21 is moved relative to the cylindrical tube 20 and on the position of the piston 21 relative to the cylindrical tube 20. A first method herein is denoted as "absolute pressure" method, whereas a second method is denoted as "relative pressure" method.

Within the "absolute pressure" method the frictional force $F_0$ is estimated using a model.

A graphical view of the (overall) force F as measured when pushing the piston 21 into the cylindrical tube 20 is shown in FIG. 4. Herein, different curves K1-K3 indicate the force F (in gram force (gf)) for different velocities of the piston 21. Curve K1 for example indicates the position dependence of the force F for a low velocity, K2 for a medium velocity and K3 for a high velocity.

As visible from FIG. 4, for a high velocity (curve K3) the force F is almost constant over the entire travel range of the piston 21. As the velocity decreases, however, the force F becomes more and more position dependent, exhibiting a bulge towards the middle of the travel range. Curve K1 for example corresponds to a velocity of $2.5 \cdot 10^{-6}$ m/s, curve K2 corresponds for example to a velocity of $2.5 \cdot 10^{-5}$ m/s, and curve K3 corresponds for example to a velocity of $2.5 \cdot 10^{-4}$ m/s.

Hence, it can be concluded that the frictional force component generally cannot be assumed as constant, but shows a strong dependency on the position as well as on the velocity by which the piston 21 is moved relative to the cylindrical tube 20.

To model the frictional force, a model can be used including a term for a velocity dependent force component $F_{0,velocity}$ and a position dependent term in the shape of a position coefficient Pos_Coef(i), i being the position of the piston 21 relative to the cylindrical tube 20, as follows:

$$F_0(i) = F_{pr} + (F_{0,velocity} - F_{pr}) \cdot Pos\_coef(i)$$

Herein, $F_0(i)$ is the frictional at the position i, $F_{pr}$ is a preload force, $F_{0,velocity}$ is the velocity dependent term, and Pos_coef(i) is the position dependent coefficient.

The velocity dependent term $F_{0,velocity}$ can be modeled according to the following equation:

$$F_{0,velocity} = F_C + (F_{brk} - F_C) \cdot e^{(-C_v \cdot v)} + f_{vfr} \cdot v$$

Herein, the first term $F_C$ represents a term for the Coulomb friction (dry friction), the second term represents the Stribeck friction and the third term represents the viscous friction. $F_{brk}$ is the breakaway force, $C_v$ is a so-called transition approximation coefficient, and $f_{vfr}$ is a viscous friction coefficient. The velocity dependent term of the frictional force is shown in FIG. 5 in dependence on the velocity v.

The parameter $C_v$ (denoted as the transition approximation coefficient) in the second term representing the Stribeck friction can be chosen for example according to curve K3 in FIG. 4, i.e. according to the minimum force at a velocity of $2.5 \cdot 10^{-4}$ m/s:

$$C_v = \frac{4}{2.5 \cdot 10^{-4} \text{ m/s}} = 1.28 \cdot 10^{-4} \text{ s/m}$$

$F_C$ is the Coulomb friction force (which is the friction that opposes motion with a constant force at any velocity) and can be described by the following equation:

$$F_C = F_{pr} + f_{cfr} \cdot P,$$

$f_{cfr}$ being the Coulomb friction Coefficient. If it is assumed that the pressure P has no impact on the friction force this becomes:

$$F_C = F_{pr}$$

and one obtains for the velocity dependent term:

$$F_{0,velocity} = F_{pr} + (F_{brk} - F_{pr}) \cdot e^{(-C_v \cdot v)} + f_{vfr} \cdot v$$

This can be simplified by neglecting the viscous effect and by applying a linearization for the Stribeck term as follows, also shown in FIG. 6:

When v [mm/h]<$v_{transit}$ [mm/h] then $$F_{0,velocity}[gf] = F_{brk}[gf]$$

When v [mm/h] ∈ [$v_{transit}$[mm/h], $v_{max}$[mm/h]] then $$F_{0,velocity}[gf] = F_{pr} + a[gf/(mm/h)] \cdot v[mm/h] + b[gf]$$

where $$\begin{cases} a[gf/(mm/h)] = \dfrac{F_{brk}[gf] - F_{pr}[gf]}{v_{transit}[mm/h] - v_{max}[mm/h]} \\ b[gf] = -a[gf/(mm/h)] \cdot v_{max}[mm/h] \end{cases}$$

When v[mm/h]>$v_{max}$[mm/h] then $$F_{0,velocity}[gf] = F_{pr}[gf]$$

Hence, when the velocity v is below a first velocity called $v_{transit}$, the velocity dependent term assumes the value of $F_{brk}$. If the velocity the is above a second velocity called $v_{max}$, the velocity dependent term assumes the value $F_{pr}$. And for a velocity in between the first velocity and the second velocity the velocity dependent term changes linearly.

In an example the parameters used in the equations may assume the values according to Table 1 as below. These parameters may for example correspond to a syringe having a volume of 5 cc.

TABLE 1

| Parameter | | Value |
|---|---|---|
| Preload force | $F_{pr}$ | 1.1 N |
| Coulomb friction Coefficient | $F_{cfr}$ | 0.1 N/bar |
| Coulomb friction force | $F_C$ | 1.1 N |
| Breakaway friction force | $F_{brk}$ | 3.2 N |
| Viscous friction coefficient | $F_{vfr}$ | 100 N/(m/s) |
| Transition approx. coeff. | $C_v$ | 1.28E+04 s/m |

The velocity dependent term is an estimate of the behavior of the frictional force $F_0$ in dependence on the velocity. To include also the influence of the position, FIGS. 7A to 7D and 8A to 8D shall be considered.

As visible from FIG. 7A to 7D, the structural characteristics in particular of the cylindrical tube 20 may vary along the travel range of the piston 21 relative to the cylindrical tube 20. In particular, the cylindrical tube 20 may not exhibit a constant diameter, but the diameter may change over position, i.e. it may decrease or increase, as shown in particular in FIG. 7B to 7D. From such structural variations, a variation of the frictional force over the position may arise, as schematically shown in FIG. 8A to 8D.

Hence, for a particular syringe of a particular model, a particular batch, a particular volume and a particular brand a very specific dependence of the frictional force on the position may arise. Hence, the dependence of the frictional force on the position is parametrized for different syringes and stored in a database of the infusion device 1 for the different syringes.

For example, a particular syringe may have a dependence of the frictional force on the position as shown in FIG. 9. This can be parameterized by storing coefficient values for discrete positions X1, X2, . . . modeling the behavior of the frictional force. For example, each syringe can be characterized by coefficient values at five points, wherein it is interpolated between the coefficient values for positions in between two neighboring points.

For example, coefficients can be stored for a position at which the syringe is fully empty (position H), for a position in which the syringe assumes its nominal capacity (position R), and at three points in between (at H+¼ (R−H), at H+½ (R−H), and at H+¼ (R−H)). For example for a 5 cc syringe these positions may equal H=13.81 mm, 24.98 mm, 36.16 mm, 47.33 mm, and R=58.5 mm.

For these points the coefficients can for example be as shown in Table 2:

TABLE 2

| Position | Position Coef | Example |
|---|---|---|
| 0 | Pos_Coef(0) | Pos_Coef(0) = 0.25 |
| 1 | Pos_Coef(1) | Pos_Coef(1) = 0.85 |
| 2 | Pos_Coef(2) | Pos_Coef(2) = 1 |
| 3 | Pos_Coef(3) | Pos_Coef(3) = 0.8 |
| 4 | Pos_Coef(4) | Pos_Coef(4) = 0.1 |

The computed velocity-and-position-dependent frictional force $F_0$ according to the equation $$F_0(i) = F_{pr} + (F_{0,velocity} - F_{pr}) \cdot Pos\_coef(i)$$

then comes out as shown in FIG. 10 for different velocities (curves F1 to F5, curve F1 corresponding to the lowest velocity and curve F5 to the highest velocity) for the example of a 5 cc syringe according to the parameters of Tables 1 and 2 as above. A close resemblance to the actually measured force F (FIG. 4) can be recognized.

In particular, it comes out that if v [mm/h]<$v_{transit}$[M m/h] then $$F_0(i)[gf] = F_{pr}[gf] + (F_{brk}[gf] - F_{pr}[gf]) \cdot Pos\_coef(i)$$

if v[mm/h] ∈ [$v_{tansit}$[mm/h], $v_{max}$[mm/h]] then $$F_0(i)[gf] = F_{pr}[gf] + (a[gf/(mm/h)] \cdot v[mm/h] + b[gf]) \cdot Pos\_Coef(i)$$

where $$\begin{cases} a[gf/(mm/h)] = \dfrac{F_{brk}[gf] - F_{pr}[gf]}{v_{transit}[mm/h] - v_{max}[mm/h]} \\ b[gf] = -a[gf/(mm/h)] \cdot v_{max}[mm/h] \end{cases}$$

and if v[mm/h]>$v_{max}$[mm/h] then $$F_0(i)[gf] = F_{pr}[gf]$$

The frictional force determined by this method can then be used for determining the pressure during an actual infusion process such that the pressure can be compared to a threshold in order to conclude whether an occlusion on the infusion line 3 is present or not.

The method is functional by itself and by itself can be used to determine the frictional force in order to get an accurate estimate of the pressure within the infusion line 3.

Another method denoted as the "relative pressure" method makes use of the assumptions that the infusion device 1 is the only pumping source acting onto the infusion line 3, and the only pressure to be observed stems from a direct occlusion.

The method relies on the principle to measure and monitor the force F necessary to push the piston 21, and to consider the measured force F as the normal frictional force $F_0$ except when the observed force evolution looks like the expected evolution in case of an occlusion.

(As the above-noted two hypotheses will not be always fulfilled, the "relative pressure" method will not give a reliable pressure value in case of for example multiline infusion systems or in case of another external device providing pressure. The "relative pressure" method hence not necessarily is meant to replace the "absolute pressure" method as described above, but may serve as in addition providing accurate results if the assumptions are true.

It is likely that for many scenarios the assumptions are fulfilled such that the method described below will give very exact and reliable results, for example for the neonatal therapy which requires a very good sensitivity and accuracy.)

In general, within the method the force is continuously measured, and in case no occlusion is present the frictional force is assumed to equal the measured force. However, if a slope of the measured force is detected which falls into a predefined range around an expected slope, it is assumed that the corresponding rise in the measured force is due to an occlusion.

This is based on the finding that an occlusion in a particular system will generally cause a rise of the measured force according to a rather well-defined slope, which can be determined when mechanical characteristics of the system such as the compliance of the infusion line 3, the compliance of the cylindrical tube 20 and the stiffness of the mechanical system of the pusher device 12 are known. If a detected slope of the measured force resembles the expected slope indicative of an occlusion, it is concluded that an occlusion may be present.

The expected slope is the theoretical slope that the pressure should follow in case the line is occluded at the catheter level. It depends on:

the flowrate, the syringe mechanical properties (especially the syringe stopper stiffness), the syringe pump mechanical properties (especially the pusher stiffness), the infusion line mechanical properties (the tube compliance).

the fluid properties (which can be neglected if it is assumed that the fluid to be pumped is an incompressible liquid).

The pressure slope can either be expressed referring to time or referring to volume. Expressing the expected slope with reference to volume, the expected slope at a position i comes out to be:

$$\text{Expected\_slope}(i)[\text{bar/ml}] = \frac{dP(i)[\text{bar}]}{dVolume(i)[\text{ml}]}$$

The expected slope is equivalent to a volumetric stiffness, which is the inverse of the system compliance. One can therefore write $$\frac{1}{\text{Volumetric\_Stiffness}[\text{bar/ml}]} = \sum_{k=1}^{3} \frac{1}{\text{Volumetric\_Stiffness}(k)[\text{bar/ml}]}$$

Where $$\begin{cases} \text{Volumetric\_Stiffness}(1)[\text{bar/ml}] = \frac{1}{\text{Syringe\_Compliance}[\text{ml/bar}]} \\ \text{Volumetric\_Stiffness}(2)[\text{bar/ml}] = \frac{1}{\text{Line\_Compliance}[\text{ml/bar}]} \\ \text{Volumetric\_Stiffness}(3)[\text{bar/ml}] = \frac{100 \cdot \text{Pusher\_Stiffness}[gf/\text{mm}]}{\text{Syringe\_Surface}[\text{mm}^2]^2} \end{cases}$$

and the expected slope comes out to be:

$$\text{Expected\_slope}[\text{bar/ml}] = \frac{1}{\text{Syringe\_Compliance}[\text{ml/bar}] + \text{Line\_Compliance}[\text{ml/bar}] + \frac{\text{Syringe\_Surface}[\text{mm}^2]^2}{100 \cdot \text{Pusher\_Stiffness}[gf/\text{mm}]}}$$

This can be converted to a slope by millimeter, assuming that for a different syringe 1 mm is equivalent to (syringe_Surface S $[\text{mm}^2]/1000$) ml:

$$\text{Expected\_slope}[\text{bar/mm}] = \frac{\text{Syringe\_Surface}[\text{mm}^2]}{1000 \cdot (\text{Syringe\_Compliance}[\text{ml/bar}] + \text{Line\_Compliance}[\text{ml/bar}]) + 10 \cdot \frac{\text{Syringe\_Surface}[\text{mm}^2]^2}{\text{Pusher\_Stiffness}[gf/\text{mm}]}}$$

We can also convert this slope to gf/mm. Assuming that for a given syringe $F[gf]=10.2*P[bar]*S[\text{mm}^2]$, the slope in bar/mm can be converted into a slope in gf/mm:

$$\text{Expected\_slope}[gf/\text{mm}] = \frac{0.0102 \cdot \text{Syringe\_Surface}[\text{mm}^2]^2}{(\text{Syringe\_Compliance}[\text{ml/bar}] + \text{Line\_Compliance}[\text{ml/bar}]) + \frac{\text{Syringe\_Surface}[\text{mm}^2]^2}{\text{Pusher\_Stiffness}[gf/\text{mm}]}}$$

Example parameter values for a 5 cc syringe of a particular brand and a particular infusion device are summarized in Table 3:

TABLE 3

| Parameter | Value |
| --- | --- |
| Syringe_Compliance | 0.0566 ml/bar |
| Line_Compliance | 0.145 ml/bar |
| Pusher_Stiffness | 9279 gf/mm |
| Syringe inner diameter | 11.87 mm |

TABLE 3-continued

| Parameter | Value |
| --- | --- |
| Syringe surface S | 110.66 mm² |

Using these parameters, the following values for the expected slope are obtained:
Expected_Slope [bar/ml]=4.65 [bar/ml]
Expected_Slope [bar/mm]=0.514 [bar/mm]
Expected_Slope [gf/mm]=568.8 [gf/mm]
This expected slope is independent of the flow rate.

Thus, it can be assumed that the expected slope in case of an occlusion will be close to 0.5 bar/mm for the particular syringe and the particular infusion device for which the parameters are valid.

To provide a range of tolerance, a maximum slope and a minimum slope shall be determined.

To determine the maximum slope the following considerations are made:

If the syringe and the infusion line were infinitly rigid, the slope would be given by the pusher stiffness and the smallest syringe:
Inner diameter=5.5 mm=>syringe_Surface S=23.76 mm²
Max_expected_slope_bar/ml=Pusher_Stiffness/(10S)=39 bar/mm
If the standard line compliance is occluded, one gets:
Max_Expected_Slope_bar/mm=0.16 bar/mm
If one considers a very rigid neonatal line with a compliance ten times lower:
Line_Compliance=0.0145 ml/bar,
one obtains:
Max_Expected_Slope_bar/mm=1.6 bar/mm This provides an estimate of the maximum slope, providing an upper boundary for a range around the expected slope.

To obtain an estimate of the minimum slope the following considerations are made:

For a large volume syringe, for example a 50 cc syringe, the compliance is about 0.8 ml/bar.
syringe_Compliance=0.64 ml/bar
Line_Compliance=0.145 ml/bar
Pusher_Stiffness=9279 gf/mm
syringe_InnerD=26.36 mm=>syringe_Surface=545.7 mm²
From these parameters one obtains for the expected slope:
Expected_Slope_bar/mm=0.49 bar/mm
Expected_Slope_gf/mm=2674 gf/mm
which is very closed to 0.51 bar/mm obtained above for a 5 cc syringe.

If one assumes a very soft syringe having a compliance three times higher than the considered 50 cc syringe and a diameter of 20 mm, and if further an extension line three times more compliant than the standard line is assumed, one obtains an estimate of a minimum expected slope as follows:
Min_Expected_Slope_bar/mm=0.12 bar/mm Hence, the range for the slope can be assumed as summarized in Table 4:

TABLE 4

| Minimum expected Slope | Typical expected slope | Maximum expected Slope |
| --- | --- | --- |
| 0.12 bar/mm | 0.5 bar/mm | 1.6 bar/mm |

During an infusion process, in particular at each start of infusion process, the expected slope is computed according to the following equation for the particular parameters of the infusion line, the syringe and the device in use:

$$\text{Expected\_slope[bar/mm]} = \frac{\text{Syringe\_Surface[mm}^2\text{]}}{1000 \cdot (\text{Syringe\_Compliance[ml/bar]} + \text{Line\_Compliance[ml/bar]}) + 10 \cdot \frac{\text{Syringe\_Surface[mm}^2\text{]}^2}{\text{Pusher\_Stiffness[}gf\text{/mm]}}}$$

In test measurements it was found that the expected slope in case of an occlusion is well distinguished from any slope that usually arises during a normal infusion process when no occlusion is present. FIG. 11 shows a measured force F over the entire travel range of a piston 21 during an infusion process in case no occlusion is present. FIG. 12 shows the derivative F' of the measured force F. As visible, the values of the derivative lie in between 150 gf/mm and +200 gf/mm, which lies well outside of the expected slope (which in the above example is at 568.8 gf/mm). In particular, the expected slope for the occurrence of an occlusion seems to be well higher than any slope observed during a regular infusion process without an occlusion being present.

Hence, it should be possible to distinguish between an occlusion (indicated by a slope close to the expected slope) and the evolution of the frictional force over the travel range of the piston 21.

Based on the expected slope and the predefined range bounding the expected slope, which are determined prior to the infusion process, the method is now carried out in the following way.

During an infusion process the force F is measured, as it is shown in FIG. 13. At the same time the slope of the measured force F is determined, for example by taking the difference between the measured force F at a current position and the position immediately prior to the current position, wherein also in averaging may take place to smooth the curve of the measured force F.

If it is found that the slope does not fall into the range between the minimum slope and the maximum slope about the expected slope as defined above, it is assumed that the frictional force $F_0$ is equal to the measured force F. The frictional force $F_0$ hence tracks the measured force F.

If it however is found that the slope falls into the range in between the minimum slope and the maximum slope about the expected slope as defined above, the frictional force $F_0$ is frozen at the measured force value at the last position X1 at which the slope did not fall into said range (see FIG. 13). The friction force $F_0$ thus obtained is used to calculate the pressure, and the calculated pressure is compared to the threshold value. If the threshold is exceeded, an alarm is triggered.

This scenario is shown in FIG. 13, where it is visible that the measured force F rises for positions beyond the position X1. Beyond the position X1, for example at the position X2, the slope Δ is within the predefined range, such that the frictional force $F_0$ is held fixed at the measured force value F associated with the position X1.

If the slope Δ of the measured force F for subsequent positions once more falls out of the range, the frictional force $F_0$ again is set to the measured force F and hence tracks the measured force F.

In this regard it is to be noted that the comparison of the slope Δ to the predetermined range bounded by the minimum slope and the maximum slope about the expected slope as defined above can be used by itself to trigger an alarm. Hence, if it is found that the slope Δ falls within the predetermined range, a so called prealarm can be triggered, warning a user at an early stage that an occlusion has occurred. This can be employed in principle independently of any of the methods described above as an independent method to trigger an occlusion alarm.

The alarm herein may be a prealarm, i.e. a low priority alarm giving an early warning, but having a smaller relevance than an actual occlusion alarm triggered when it is found that an occlusion is present with a high level of confidence.

The "absolute pressure" method as described above and the relative pressure method as described above may beneficially be used in combination. The relative pressure method may offer an increased accuracy in case the assumptions on which the method are based (no other infusion devices present and no other sources causing a rise of pressure than an occlusion) are true. In case the assumptions are not true, the absolute pressure method may offer a reliable detection of an occlusion.

The invention is not limited to the embodiments described above, but may be carried out in an entirely different way.

In particular, it is not actually necessary that the pressure is calculated, but it generally is sufficient to determine a value proportional to (or generally indicative of) the pressure, which can then be compared to a suitable threshold for determining whether an occlusion has occurred.

Also, within the method as described above generally position and time can be interchanged. At a constant velocity position and time are linearly dependent.

LIST OF REFERENCE NUMERALS

1 Infusion device
10 Housing
11 Receptacle
110 Fixation device
12 Pusher device
120 Guide device
121 Connecting rod
2 syringe
20 Cylinder tube
200 Connector
21 Piston
210 Piston head
211 Piston member
3 Infusion line
χ Slope
F (Measured) force
F' Derivative of measured force
F1-F5 Curve of friction force
K1-K3 Curves
P Pressure
S Surface
X, X' Movement direction
X1, X2 Position

The invention claimed is:

1. A method for detecting an occlusion in an infusion line connected to an infusion device, comprising:
measuring a force applied to a piston by a pusher device of an infusion device during an infusion operation performed by the infusion device for moving the piston along a movement direction into a cylindrical tube in order to deliver a medical fluid from the cylindrical tube towards an infusion line connected to the cylindrical tube,
calculating, from the measured force, a value indicative of a pressure in the cylindrical tube, wherein for calculating said value indicative of said pressure a frictional force value indicative of a friction of the piston relative to the cylindrical tube is taken into account,
comparing said value indicative of said pressure to a threshold value to determine whether an occlusion is present in the infusion line during the infusion operation performed by the infusion device,
wherein the frictional force value is determined using a mathematical model modelling the friction of the piston relative to the cylindrical tube in dependence on a position of the piston relative to the cylindrical tube along the movement direction and in dependence on a velocity by which the piston is moved relative to the cylindrical tube.

2. The method according to claim 1, wherein the model includes a velocity dependent term modelling the dependence of the frictional force on the velocity of the piston relative to the cylindrical tube and a position dependent term modelling the dependence of the frictional force on the position of the piston relative to the cylindrical tube.

3. The method according to claim 2, wherein the model models the velocity dependent term by using an equation including terms for a Coulomb friction, a Stribeck friction and/or a viscous friction.

4. The method according to claim 2, wherein the velocity dependent term, for a velocity below a first velocity value and/or for a velocity above a second velocity value, assumes a constant value.

5. The method according to claim 2, wherein the velocity dependent term, for a velocity in between a first velocity value and a second velocity value, linearly changes in dependence on the velocity.

6. The method according to claim 2, wherein the position dependent term includes a position-dependent coefficient, which is multiplied with a term including the velocity dependent term to obtain the frictional force value for a current position of the piston relative to the cylindrical tube.

7. A method for detecting an occlusion in an infusion line connected to an infusion device, comprising:
measuring a force applied to a piston by a pusher device of an infusion device during an infusion operation performed by the infusion device for moving the piston along a movement direction into a cylindrical tube in order to deliver a medical fluid from the cylindrical tube towards an infusion line connected to the cylindrical tube,
calculating, from the measured force, a value indicative of a pressure in the cylindrical tube, wherein for calculating said value indicative of said pressure a frictional force value indicative of a friction of the piston within the cylindrical tube is taken into account,
comparing said value indicative of said pressure to a threshold value to determine whether an occlusion is present in the infusion line during the infusion operation performed by the infusion device,
determining, at a current position of the piston, a slope value associated with the measured force at the current position of the piston as the piston is moved along the movement direction, and
if the slope value lies within a predetermined range, assuming that the frictional force value is equal to the measured force at a position prior to the current position for calculating said value indicative of said pressure.

8. The method according to claim 7, wherein said position prior to the current position is a position for which the slope value is outside of the predetermined range.

9. The method according to claim 7, wherein the slope value is determined from the difference of the measured force at the current position and the measured force at a position prior to the current position.

10. The method according to claim 7, wherein, if the slope value does not lie within said predetermined range, the frictional force value is assumed to equal the measured force at the current position of the piston.

11. The method according to claim 7, wherein the predetermined range is bounded by a minimum slope smaller than an expected slope and a maximum slope larger than the expected slope.

12. The method according to claim 7, wherein the expected slope is determined taking a compliance of the cylindrical tube, a compliance of the infusion line, a stiffness of the pusher device and/or a dimension of the cylindrical tube into account.

13. The method according to claim 12, wherein values for the compliance of the cylindrical tube, the compliance of the infusion line, the stiffness of the pusher device and/or the dimension of the cylindrical tube are stored in the infusion device for at least one syringe used on the infusion device.

14. The method according to claim 7, wherein a prealarm is triggered if the slope value lies within a predetermined range.

15. A method for detecting an occlusion in an infusion line connected to an infusion device, comprising
(a) measuring a force applied to a piston by a pusher device of an infusion device for moving the piston along a movement direction into a cylindrical tube in order to deliver a medical fluid from the cylindrical tube towards an infusion line connected to the cylindrical tube,
calculating, from the measured force, a value indicative of a pressure in the cylindrical tube, wherein for calculating said value indicative of said pressure a frictional force value indicative of a friction of the piston relative to the cylindrical tube is taken into account,
comparing said value indicative of said pressure to a threshold value to determine whether an occlusion is present in the infusion line,
wherein the frictional force value is determined using a mathematical model modelling the friction of the piston relative to the cylindrical tube in dependence on a position of the piston relative to the cylindrical tube along the movement direction and in dependence on a velocity by which the piston is moved relative to the cylindrical tube;
and
(b) measuring a force applied to a piston by a pusher device of an infusion device for moving the piston along a movement direction into a cylindrical tube in order to deliver a medical fluid from the cylindrical tube towards an infusion line connected to the cylindrical tube,
calculating, from the measured force, a value indicative of a pressure in the cylindrical tube, wherein for calculating said value indicative of said pressure a frictional force value indicative of a friction of the piston within the cylindrical tube is taken into account,
comparing said value indicative of said pressure to a threshold value to determine whether an occlusion is present in the infusion line,
determining, at a current position of the piston, a slope value associated with the measured force at the current position of the piston as the piston is moved along the movement direction, and
if the slope value lies within a predetermined range, assuming that the frictional force value is equal to the measured force at a position prior to the current position for calculating said value indicative of said pressure,
wherein the steps of (a) and (b) are carried out in parallel during an infusion operation performed by the infusion device.

16. The method according to claim 15, wherein an alarm is triggered if it is determined with at least one of (a) and (b) that said value indicative of the pressure is above said threshold value.

* * * * *